US006005078A

United States Patent [19]

Rooney

[11] Patent Number: 6,005,078

[45] Date of Patent: Dec. 21, 1999

[54] CANINE-DERIVED HEMOGLOBIN BLOOD SUBSTITUTE, THE PROCESS FOR PREPARING SAME AND USES THEREOF

[76] Inventor: Michael William Rooney, 202 Arron Ct., Vernon Hills, Ill. 60061

[21] Appl. No.: 08/645,744

[22] Filed: May 14, 1996

[51] Int. Cl.$^6$ .................................................... A61K 35/14

[52] U.S. Cl. ................................... 530/385; 514/6; 514/2

[58] Field of Search ................................ 530/385; 514/2, 514/6

[56] References Cited

U.S. PATENT DOCUMENTS 5,084,558 1/1992 Rausch et al. .......................... 530/385

OTHER PUBLICATIONS

Sigma on–line catalog. Product information. Product #H7130.

*Primary Examiner*—Cecilia J. Tsang
*Assistant Examiner*—Michael Borin

[57] ABSTRACT

A canine-derived hemoglobin blood substitute comprising an extract of dog erythrocyte cytoplasm in a pharmaceutically acceptable carrier, the process for preparing the same and uses thereof. The process comprises utilizing membrane molecular phase transitions to induce and reverse a nonporous-porous behavior of erythrocytes, conserving all membrane and cytoskeletal material as well as all cytoplasmic enzymes including methemoglobin-reducing enzymes, yielding large quantities that do not require dialysis to remove potassium, and steps to easily prepare and use the product without extensive processing or chromatographic separation. In contrast to the prior art, the canine-derived blood substitute does not exhibit hypertension, vasoconstriction or loss of blood volume. The homologous product is intended for treatment of diseases or medical conditions of dogs requiring an increase, restoration or supplement in oxygen perfusion without hemodynamic or immunologic restriction.

8 Claims, 11 Drawing Sheets

CANINE-DERIVED HEMOGLOBIN BLOOD SUBSTITUTE, THE PROCESS FOR PREPARING SAME AND USES THEREOF

A portion of the disclosure of this patent document contains material which is subject to copyright protection. The copyright owner has no objection to the facsimile reproduction by any one of the patent disclosure, as it appears in the Patent & Trademark Office patent files or records, but otherwise reserves all copyright rights whatsoever.

FIELD OF THE INVENTION

The present invention relates to a process for preparing a canine-derived hemoglobin blood substitute. More particularly, the present invention relates to a novel method for obtaining from dog erythrocytes an uncontaminated cytoplasmic extract that is free of membrane or membrane-associated cytoskeletal material, that contains natural methemoglobin-reducing systems, that does not require dialysis or adjustment of potassium concentration, and that is easily prepared and usable without extensive processing. The invention demonstrates that the blood substitute extract, diluted in a pharmaceutically acceptable carrier medium, is safe, efficacious and provides enablement for its use in canine patients in need of increased oxygen perfusion either systemically or to regional organs, especially heart and skeletal muscle, without the hypertension (vasoconstriction) produced by all prior art hemoglobin blood substitutes and, because it is homologous, has less risk of immunological incompatibility.

BACKGROUND

There are many veterinary medical conditions, for example hemorrhagic hypotension and anaphylactic shock, in which significant blood loss and/or hypotension (abnormally low blood pressure) occur leading to tissue hypoxia. For subjects with such medical conditions, it is desirable and often critical for their survival to stabilize their blood pressure and to increase the amount of oxygen provided to body tissues by their circulatory systems.

Considerable effort has therefore been expended in developing substances which may be used as resuscitation fluids and/or blood plasma expanders for stabilizing blood pressure and which are capable of carrying and delivering oxygen to bodily tissues. While transfusion of whole blood or commercially prepared red blood cells (packed) may stabilize blood pressure and provide the needed oxygen for survival, there are many costs (blood-typing; testing for antigens/antibodies, viruses and bacteria; processing expense, etc.) and risks (adverse effects on hematology or immunology; pathological organisms, etc.) associated with these therapies. Therefore, the research and development of an alternate oxygen-carrying substance is being pursued in many countries for applications in the transfusion marketplace as well as for novel therapies for many disease conditions.

Hemoglobin, the natural respiratory protein of erythrocytes which carries oxygen to body tissues from the lungs and carbon dioxide from the tissues to the lungs, is a potential alternate oxygen-carrying substance. Erythrocytes contain approximately 34 grams of hemoglobin per 100 ml of cells.

Since native hemoglobin is readily oxidized in air, commercially available preparations may comprise up to 75% methemoglobin, with the balance being primarily oxyhemoglobin (Sigma Chemical Company, St. Louis, Mo., 1996). The high methemoglobin content limits the usefulness of these preparations for use in a blood substitute or organ preservative as well as for use as a diagnostic or biochemical reagent simply because of the cost and labor required to convert or maintain methemoglobin at acceptable minimum concentrations.

Various methods have been developed to isolate hemoglobin from erythrocytes. Bonsen et al., U.S. Pat. No. 4,001,401 (issued Jan. 4, 1977) describes purifying hemoglobin by lysing red blood cells with toluene and then filtering the lysate through diatomaceous earth filters followed by dialysis. Simmonds et al., U.S. Pat. No. 4,401,652 (issued Aug. 30, 1983) and Tye et al., U.S. Pat. No. 4,473,494 (issued Sep. 25, 1984) disclose purification methods involving selective precipitation of hemoglobin with ions followed by ultrafiltration or dialysis. Hsia, U.S. Pat. No. 4,925,574 (issued May 15, 1990) describes purification of hemoglobin by affinity chromatography. Sheffield et al., Biotechnology and Applied Biochemistry, 9, 230–238 (1987) describe the dialysis of red blood cells using a hypotonic solution followed by ultrafiltration through hollow fibers. Finally, Rausch et al, U.S. Pat. No. 5,084,558 (issued Jan. 28, 1992) disclose the use of high performance liquid chromatography to isolate hemoglobin from erythrocytes.

The foregoing methods all have shortcomings in that they are time-consuming and labor-intensive, requiring multiple extraction, dialysis or filtration steps, but most importantly all require a costly postpurification reconcentration step to obtain the resulting hemoglobin solution. Additionally, the foregoing methods eliminate redox enzymes responsible in vivo for maintaining the hemoglobin in a "useful" state. In the absence of these enzymes, hemoglobin is oxidized to methemoglobin which is not capable of binding oxygen. Furthermore, the above inventions do not take advantage of dog red cell physiology which, because of the relative absence of intracellular potassium, allows for quicker and cleaner preparation of a blood substitute because no dialysis step is required to remove a potentially toxic potassium ion. In addition, this dialysis step is required in all prior art and, because dialysis removes numerous small molecular weight compounds, will thereby introduce an alteration of the natural components of the cytoplasmic extract. Another advantage of deriving a canine blood substitute from dog erythrocytes is the homologous basis of the product, i.e., there will be less risk of immunological incompatibility with proteins derived from the same species, especially when these proteins are planned for intravenous infusion in large quantities as part of a blood substitute. Immunological effects of heterologous hemoglobin blood substitutes are a central concern because of the inherent antigenicity of hemoglobin (Yoshioka et al., Biochem. J., 234, 441–447 (1986); Garver et al., Biochem. Genet., 13, 743–757 (1975). Furthermore, the prior art has demonstrated amplified antigenicity with heterologous hemoglobin that has been polymerized or cross linked (Chang et al., Biomat. Artif. Cells Immobilization Biotechnol., 20, 611–618 (1992); Viazova et al., Biull Exsp. Biol. Med., 106, 446–448 (1988); Hertzman et al., Int. J. Artif. Organs, 9, 179–182 (1986). Finally, an adverse side effect of hemoglobin blood substitutes is vasoconstriction or hypertension which may be related to a specific impurity or contaminant of the formulation or may be caused by some unique pharmacology or structure of the hemoglobin in the formulation. Whether the hypertension or vasoconstriction is caused by, or is amplified by, heterologous hemoglobin is as yet uncertain. However, recent studies with a bovine hemoglobin blood substitute in dogs, cats and humans all produced similar vasoconstriction or hypertension (Standl et al., Intensive Care Med., 23, 865–872 (1997); Ulatowski et al., Crit. Care Med., 24, 558–565 (1996); Standl et al., Anaesthetist, 46, 763–770 (1996). In view of the above presentation, it becomes immediately apparent that several needs exist in the development of a canine-derived hemoglobin blood substitute: a method of preparation that poses less risk for contamination either by membrane, membrane-associated cytoskeletal material or by extra processing steps currently used in the art, a method that preserves the endogenous or natural enzymes of the erythrocyte including methemoglobin-reducing substances, a method that, in general, has a large yield with less steps and less cost, a method that produces a canine-derived hemoglobin blood substitute that is immunologically safer with less risk of incompatibility and a method that produces a canine-derived hemoglobin blood substitute that is more efficacious without adverse restriction on blood flow and oxygen delivery that will occur with vasoconstriction or hypertension.

SUMMARY OF THE INVENTION

The present invention provides for a fast, efficient method for preparing a canine-derived hemoglobin blood substitute from dog erythrocytes. The resultant product comprises homologous hemoglobin which is concentrated (10 gm %), less than 1% methemoglobin, nonpyrogenic, sterile and free of stroma (i.e., free of erythrocyte membrane fatty acids, phospholipids and proteins). Additionally, the present invention provides for methods of treatment for diseases and medical conditions in need of replacement, restoration or supplementation of oxygen perfusion of organs, tissue or of the systemic circulation, with or without need for hemodilution, resuscitation or blood plasma expansion.

Methods according to the invention for preparing the canine-derived hemoglobin blood substitute generally comprise (a) washing a first volume of erythrocytes with room temperature saline-hetastarch solution; (b) adding a second volume of buffer (about pH 9.6) not more than twice the first volume of erythrocytes to induce a membrane molecular phase transition that results in a porous erythrocyte membrane which generally has one large hole through which cytoplasm is free to diffuse out of the erythrocyte into the second buffer to form a mixture having a hemoglobin concentration of about 11 gm % to 12 gm %; (c) stirring the mixture of step (b) for 5 minutes; (d) centrifuging the mixture of step (c) to sediment the porous erythrocytes into a pellet and thereby allow isolation of a first supernatant containing cytoplasmic extract and unsedimented porous erythrocytes; (e) adjusting electrolytes of the first supernatant to isotonicity thereby reversing the porous molecular phase transition of unsedimented erythrocyte membranes to form reconstituted nonporous erythrocytes; (f) centrifuging the mixture of step (e) to sediment reconstituted erythrocytes into a pellet and thereby allow isolation of a second supernatant containing cytoplasmic extract and unsedimented particulate material; and (g) filtering the extract of step (f) to remove unsedimented particulate material to yield the canine-derived hemoglobin blood substitute.

Preferably, method step (a) comprises serial washings with phosphate-buffered saline-hetastarch solution at a pH of about 7.4. Albumin or other colloidal electrolytes that may adhere to the membrane surface and facilitate membrane-membrane interaction during steps (b) and (c) and thereby promote sedimentation in step (d) may be substituted.

The buffer of step (b) is preferably sodium phosphate buffer at a molarity of about 5 mM and pH of about 9.6. The pH may be lowered to pH 8.0 but additional membrane-stabilizing substances should be added such as magnesium or calcium.

Preferably, the centrifugation of step (d) is performed at $3.4\times10^6$ g·minute and, more preferably, at 28,000 g for about 2 hours at 4° C. Similarly, the centrifugation of step (f) is preferably performed at $1.7\times10^6$ g·minute and, more preferably, at 28,000 g for about 1 hour at 4° C.

In step (e) sufficient sodium chloride, potassium and calcium chloride are added to result in a concentration of sodium chloride in the supernatant preferably between about 145 mM and about 155 mM, potassium chloride between about 2 mM and 4 mM, and calcium chloride between about 1 mM and 3 mM. More preferably, sufficient sodium chloride is added to result in a concentration of sodium chloride in the supernatant of about 150 mM, potassium chloride is added to result in an concentration of about 3 mM, and calcium chloride is added to result in a concentration of about 2 mM. Other physiologic resealing chemicals, (e.g., electrolytes) may be substituted for sodium chloride.

Filtration of the hemoglobin solution obtained in step (g) is also contemplated by the present invention. Preferably, the hemoglobin solution of step (g) is passed at a flow rate of about 250 ml/minute through a series of filters beginning with at most a 5$\mu$ pore size filter, next using about a 1$\mu$ pore size filter, and ending with at least a 0.25 $\mu$ pore size filter.

Although the erythrocytes subjected to the purification methods may be obtained from any mammalian source (e.g., bovine, ovine or porcine erythrocytes) including humans, the present invention is optimal with canine erythrocytes because of the natural low potassium content of erythrocytes in this species. Supernatant obtained from human erythrocytes or animals other than canine, including transgenic animals, may require more costly removal of unwanted potassium ions or further adjustment of electrolyte concentrations.

The canine-derived hemoglobin blood substitute of the methods of the present invention is homologous, concentrated, sterile, nonpyrogenic, lipid-free, uncontaminated by membrane or membrane-associated cytoskeletal material, comprised of cytoplasmic enzymes including methemoglobin-reducing enzymes, non-dialyzed, not chromatographically separated and retains original cytoplasmic potassium. The product of the present invention may be used without further processing steps, and may be used as, or in, a commercial biochemical or biological system, or in a commercial in vitro or in vivo organ perfusion product.

Regarding its use for other commercial therapeutic compositions, the process of the present invention may be applied to other mammalian erythrocytes. The hemoglobin blood substitute product from dog or other mammalian erythrocytes may be modified to prevent rapid clearance from the intravascular space in vivo. For example, the hemoglobin blood substitute products may be cross-linked, chemically modified with compounds such as polyethylene glycol or may be encapsulated, for example, in liposomes, glucose polymers or gelatin.

Therapeutic compositions according to the present invention were administered, without further modification, in large doses (50% of blood content) to dogs to sustain cardiac output, normal blood pressure, i.e. no hypertension, and wholebody oxygen delivery.

The therapeutic hemoglobin compositions of the present invention may be described as "blood component substitutes." In addition to hemoglobin, the compositions may include physiologically acceptable plasma substitutes. Suitable plasma substitutes are linear polysaccharides (e.g., dextrans, gum arabic pectins, balanced fluid gelatin, and hydroxyethyl starch), polymeric substitutes (e.g., polyethylene oxide, polyacrylamide, polyvinyl pyrrolidone, polyvinyl alcohol, ethylene oxide-propylene glycol condensate), aqueous solutions (e.g., Lactated Ringers and saline), coacervates (composed of fatty acids, phospholipids, glycerates or cholesterol, for example) and colloidal substitutes (e.g., albumin).

The therapeutic compositions according to the present invention are useful for treatment of diseases or medical conditions in which intravascular or intraosseous administration of a resuscitative fluid or blood plasma expander is indicated/required. Resuscitative fluids and blood plasma expanders are required for treatment of diseases and medical conditions in which there is significant blood loss, hypotension and/or a need to maximize the availability of oxygen to the body tissues. Examples of such diseases and medical conditions are hemorrhagic hypotension, septic shock, cardiopulmonary bypass, neoplastic anemias, plasma and extracellular fluid loss from burns, stroke, angioplasty, cardioplegia, radiation therapy, acute myocardial infarction, and both routine and lengthy surgical procedures.

Methods of treating such veterinary diseases and medical conditions according to the present invention comprise the step of administering to a dog, or other mammal with a homologous hemoglobin blood substitute derived by the process of the present invention, the product of the invention process to restore, replace or supplement oxygen perfusion to regional organs or to the general systemic circulation.

Examples of the present invention demonstrate that administration of the canine-derived hemoglobin blood substitute to dogs according to hemodilution conventions in the art, for example, as described in Messmer et al., Prog. Surg., 13, 208–245 (1974), result in increased oxygen perfusion selectively to skeletal and heart muscle without the vasoconstriction produced by the prior art, and without the systemic hypertension produced by the prior art.

DETAILED DESCRIPTION

Figure 1A:
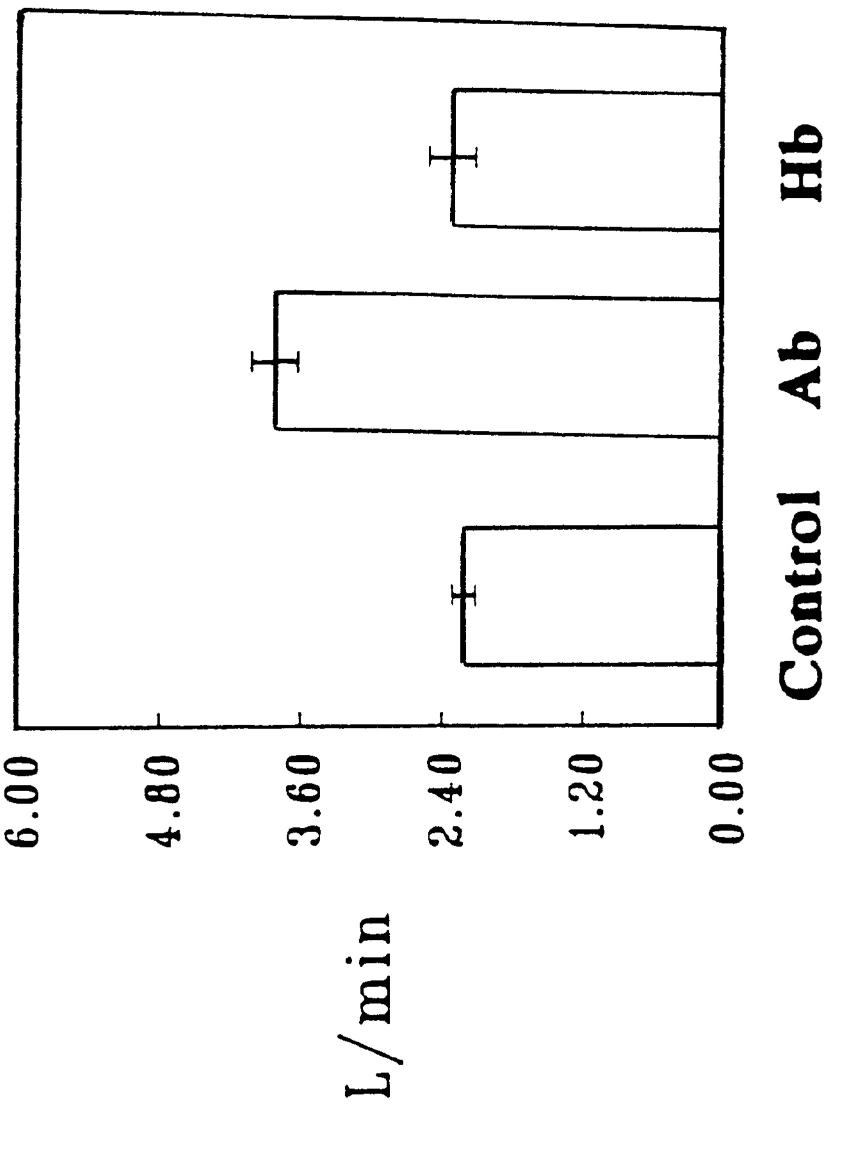
FIG. 1A is bar graph representing the cardiac output (L/minute) of control baseline, albumin-hemodilution (AB), and hemoglobin-hemodilution (Hb) in mongrel dogs.
Figure 1B:
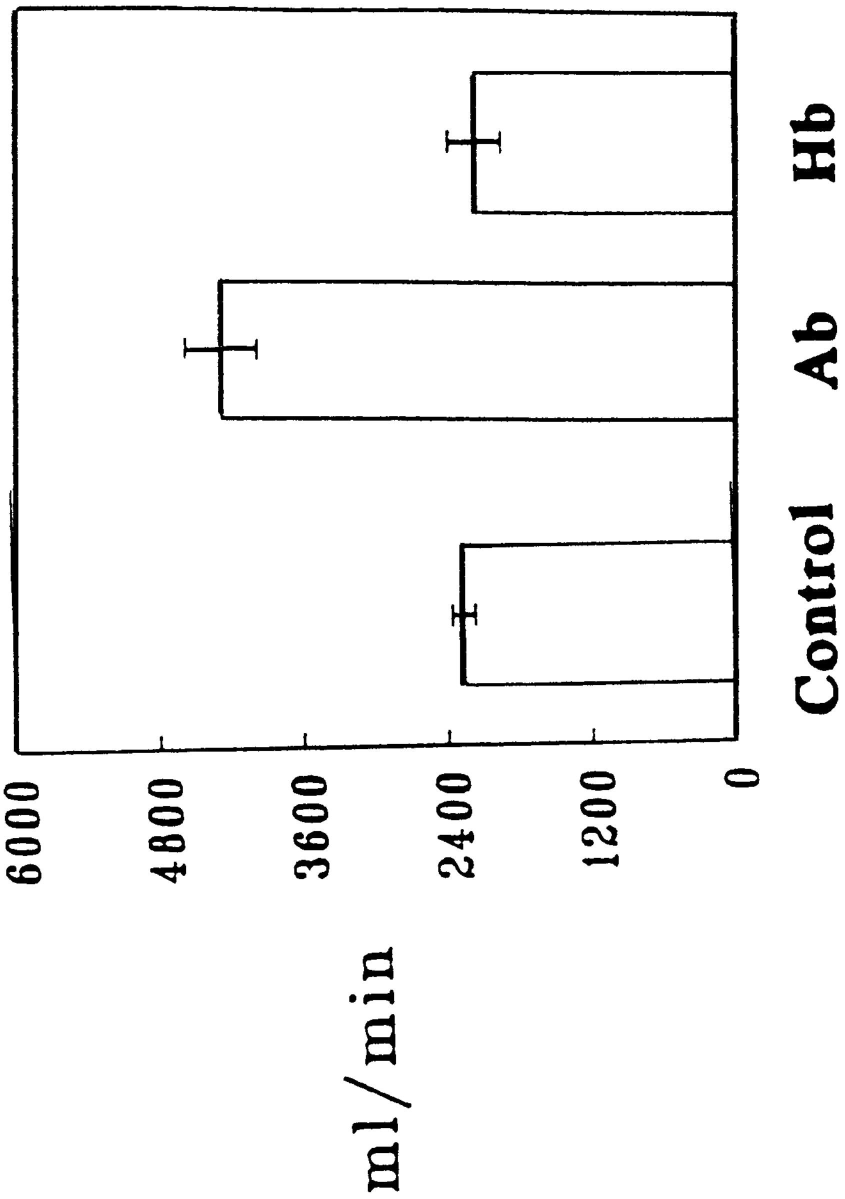
FIG. 1B is a bar graph representing the sum of regional blood flows (ml/minute) of control baseline, albumin-hemodilution (AB), and hemoglobin-hemodilution (Hb) in mongrel dogs.
Figure 1C:
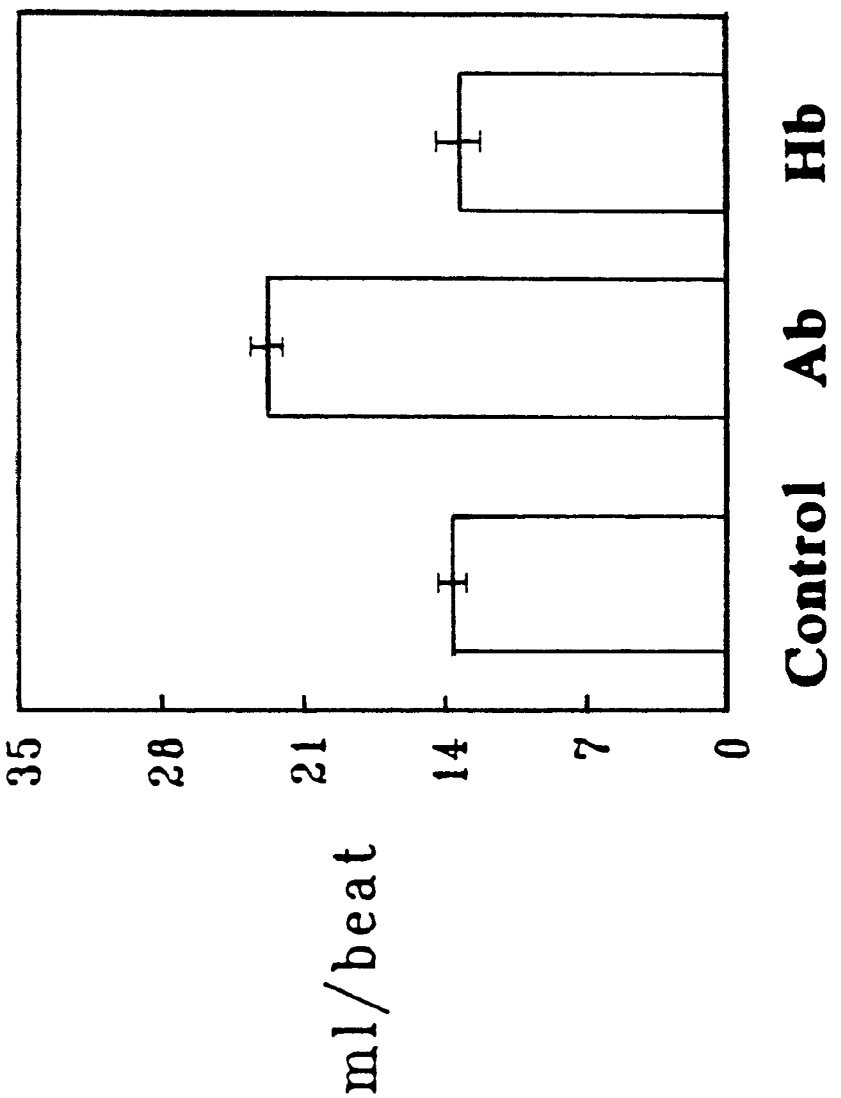
FIG. 1C is a bar graph representing the stroke volume (ml/beat) (computed from cardiac output) of control baseline, albumin-hemodilution (AB), and hemoglobin-hemodilution (Hb) in mongrel dogs.
Figure 1D:
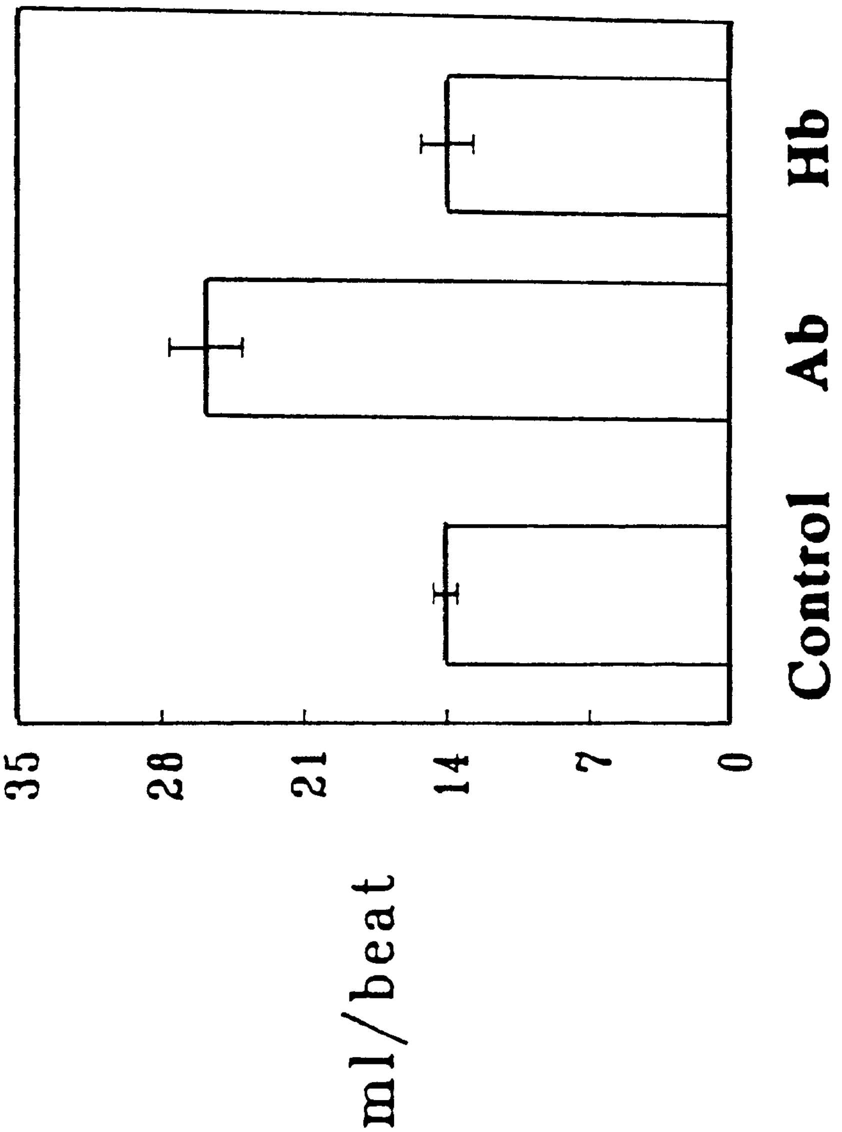
FIG. 1D is a bar graph representing the stroke volume (ml/beat) (computed from sum of regional blood flows) of control baseline, albumin-hemodilution (AB), and hemoglobin-hemodilution (Hb) in mongrel dogs.
Figure 2A:
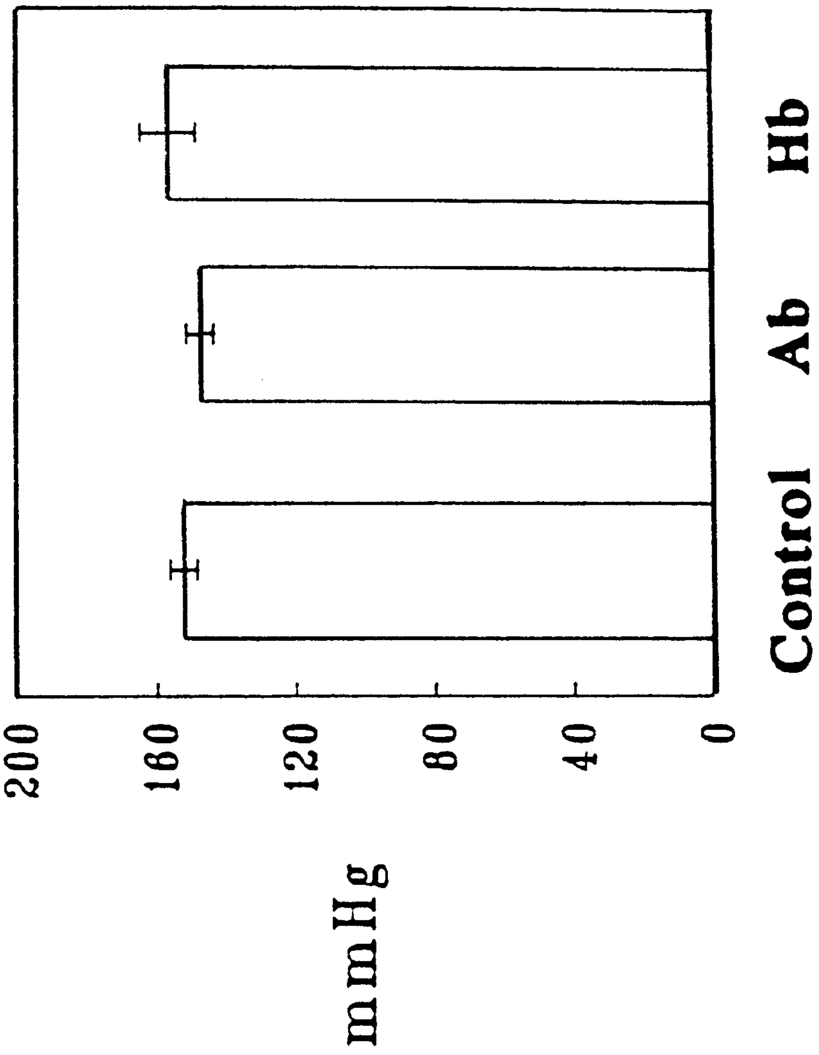
FIG. 2A is a bar graph representing the systolic aortic pressure (mmHg) of control baseline, albumin-hemodilution (AB), and hemoglobin-hemodilution (Hb) in mongrel dogs.
Figure 2B:
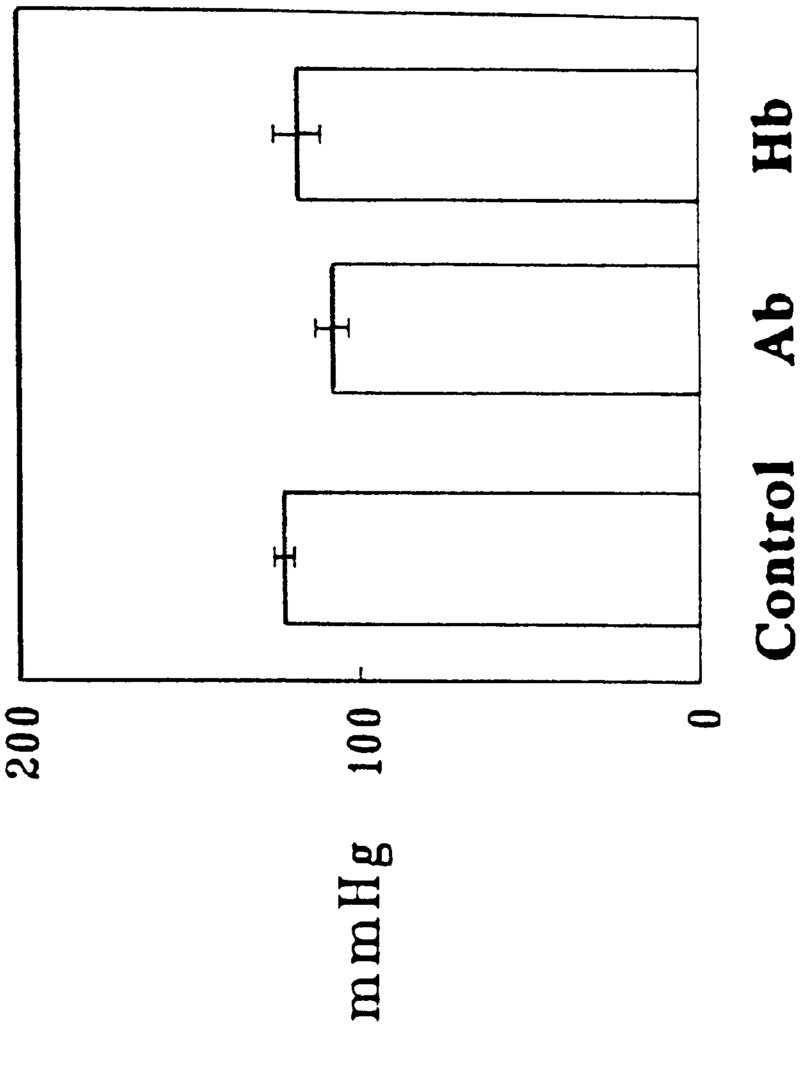
FIG. 2B is a bar graph representing the diastolic aortic pressure (mmhg) of control baseline, albumin-hemodilution (AB), and hemoglobin-hemodilution (Hb) in mongrel dogs.
Figure 2C:
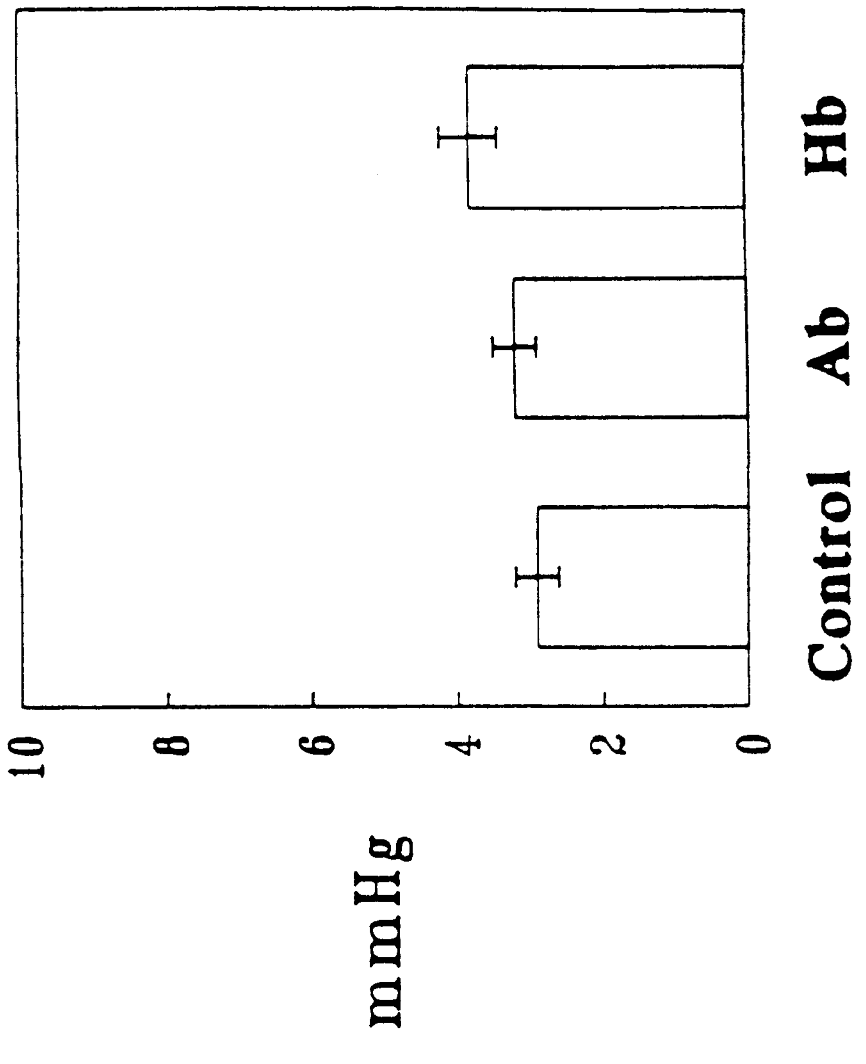
FIG. 2C is a bar graph representing the right atrial pressure (mmHg) of control baseline, albumin-hemodilution (AB), and hemoglobin-hemodilution (Hb) in mongrel dogs.
Figure 2D:
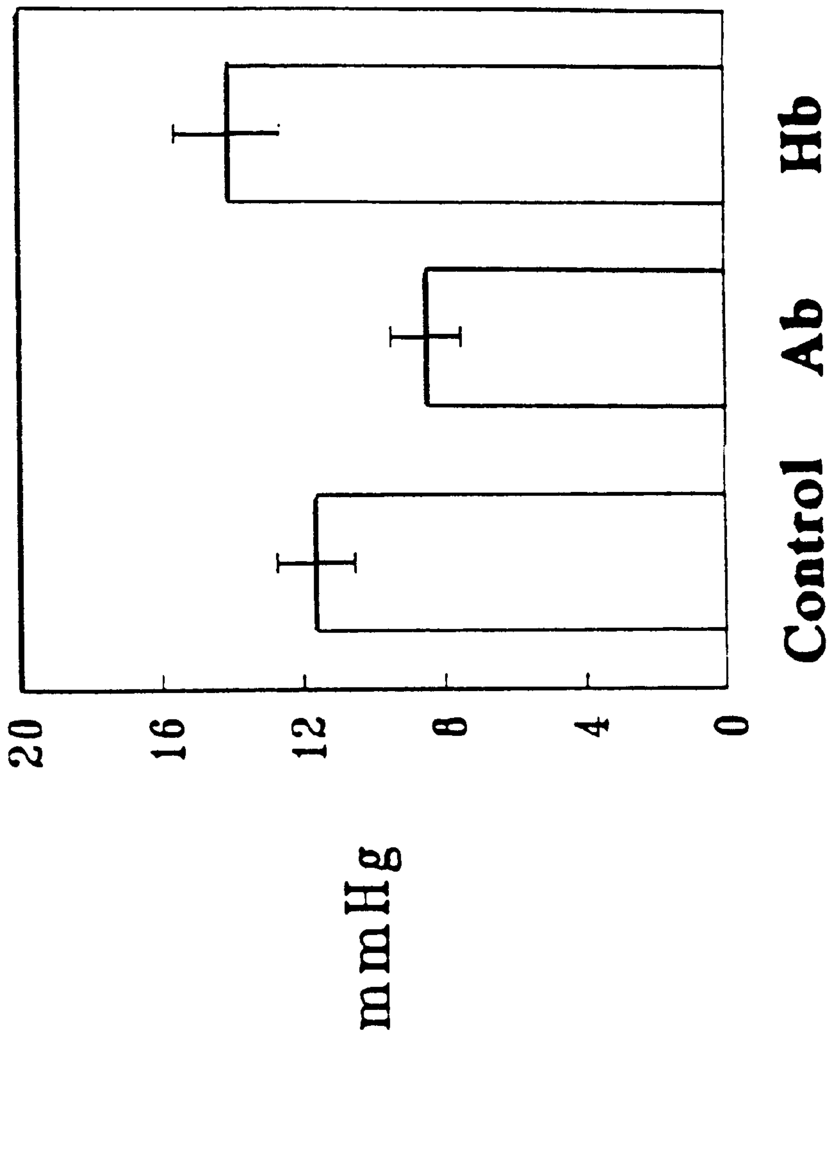
FIG. 2D is a bar graph representing the left ventricular end-diastolic pressure (mmHg) of control baseline, albumin-hemodilution (AB), and hemoglobin-hemodilution (Hb) in mongrel dogs.

The following examples illustrate practice of the invention in preparing a canine-derived hemoglobin blood substitute from dog erythrocytes and in treating dogs with said blood substitute to demonstrate its specific uses, effectiveness and safety.

EXAMPLE 1

Erythrocytes were obtained from anesthetized adult mongrel dogs by arterial cannulation under aseptic operating room conditions. In agreement with standard blood-banking practices, 60 ml of sterile citratephosphate-dextrose-adenine (CPDA) preservative anticoagulant was added to every 500 ml of whole blood. Also added were a gram-negative antibiotic and a grampositive antibiotic. The blood was then stored in sterile, pyrogen-free containers at 4° C. Upon removal of the blood from storage, plasma and white cells were removed by standard procedures described in McCarthy et al., Eds., *Controversies of Leukocyte-Poor Blood and Components*, Arlington, Virginia, American Association of Blood Banks (1989).

The canine-derived hemoglobin blood substitute was prepared from the red blood cells by the following steps. The cells, previously packed with centrifugation at 1500×g for 20 minutes at 4° C., were washed 3 times with phosphate-buffered saline-hetastarch solution (pH 7.4), alternately adding 2 volumes of buffer with packed cells, mixing gently, and packing with centrifugation at 1500×(g) for 20 minutes at 4° C. The buffer phosphate content was 5 mM, saline was normal (0.9%) and the hetastarch was 6 gm %. All solutions utilized were sterile. Next, 1200 ml of 5 mM dibasic sodium phosphate buffer (pH 9.6) was added to 600 ml of packed red cells, bringing the hemoglobin concentration of the mixture to about 11.5 gm %. The mixture was stirred slowly for 10 minutes. These steps induce a molecular phase transition in the wall of the red blood cell membrane to create a porous, molecularly stable membrane through which cytoplasm may diffuse out to the extracellular aqueous. During the transition to a porous state, membrane material is conserved such that the surrounding aqueous is not contaminated with membrane and membrane-associated cytoskeletal material (see these structures in FIGS. 4A and 4B by Bennett Physiological Reviews, 70:1029–1965, 1990).

The methods of the present invention do not disrupt the complex structure of the membrane and membrane-associated cytoskeletal material but rather typically result in the formation of a single large hole through which cytoplasmic material diffuses, leaving behind intact red cell membranes termed "ghosts" and "partial ghosts." Ghosts are devoid of most of the cytoplasm while partial ghosts contain some cytoplasm. The potential contaminants shown in FIG. A include the lipid bilayer (i.e., glycolipid, phospholipid and cholesterol), band 3, glycophorin C, spectrin, actin, ankyrin, tropomyosin, protein 4,1 and adducin. The mixture was then placed in clear polycarbonate tubes and centrifuged at 28,000×(g) for at least 2.5 hours at 4° C. to pellet ghosts and partial ghosts. Given the high density of the mixture, use of a high intensity lamp was required to visualize the resulting pellet and to isolate the supernatant (the "first supernatant").

Sufficient sodium chloride was then added to the first supernatant to result in a 150 mM for sodium chloride. Upon addition of the salt, the color of the solution changed from dark cherry red to a brighter red but more opaque solution, indicating the formation of resealed red cell membranes. These cellular structures are no longer true erythrocytes or true ghosts and a new termed will be used to identify them as "reconstituted erythrocytes." The membrane of each reconstituted erythrocyte has undergone a reverse molecular transition from the porous state back to the original nonporous state and, hence, the observation of opaque light refraction typically seen with natural blood cells. Physiological adjustments were made in potassium chloride and calcium chloride, yielding amounts about 3.0 mM and 2.0 mM respectively. The solution was mixed with a stir bar for 5 minutes and then centrifuged at 28,000 g for one hour at 4° C. These steps resulted in the resealing of ghost membranes in the first supernatant which then refract light as intact red blood cells. The mass of these resealed intact blood cells allow their sedimentation and separation from the first supernatant during centrifugation. The resulting "second supernatant" was a dark cherry red. The second supernatant was then isolated and passed through a series of filters starting with 5.0$\mu$ pore size, then continuing with 1.0$\mu$, 0.45$\mu$, and finally 0.25$\mu$ to remove any residual red cells and/or particulate matter.

The method does not contaminate the intracellular contents but rather extracts the uncontaminated cytoplasm in a pharmaceutically acceptable carrier medium. The method produces a canine-derived blood substitute product that is concentrated (10 gm %) canine hemoglobin, sterile, nonpyrogenic, lipid-free, free of membrane and membrane-associated cytoskeletal material, less than 1% methemoglobin, and comprised of the original cytoplasmic enzymes including methemoglobin-reducing enzymes as follows:

| | |
|---|---|
| enolase | superoxide dismutase |
| catalase | lactate dehydrogenase |
| hexokinase | phosphoglycerate kinase |
| transaldolase | cytochrome $b_5$ reductase |
| transketolase | diphosphoglycerate mutase |
| transaminase | pyrimidine 5'-nucleotidase |
| pyruvate kinase | lysolecithin acyl transferase |
| phosphofructokinase | glucosephosphate isomerase |
| adenosine deaminase | glutamyl-cysteine synthetase |
| phosphate isomerase | adenosine triphosphatase triose |
| glutathione reductase | diphosphoglycerate phosphatase |

-continued

| | |
|---|---|
| glutathione peroxidase | glucosephosphate dehydrogenase |
| glutathione synthetase | phosphogluconate dehydrogenase |

The diluted extract contains, among other natural cytoplasmic substances, sodium, potassium, chloride, magnesium, bicarbonate, calcium, phosphate, adenosinetriphosphate, adenosinediphosphate, glucosephosphate, fructosephosphate, sulphate, acetate, gluconate, pyruvate, lactate, glucose, adenine, nicotinamide adenine dinucleotide, nicotinamide adenine dinucleotide phosphate, diphosphoglycerate, cysteine, glycine, glutamate, and glutathione. The diluted extract had no detectable lipid content determined with U.S. EPA method 413.2 (lower limit 200 nanogram per milliliter) and was not dialyzed or chromatographically-separated to remove or adjust components and contains the original cytoplasmic potassium plus added potassium.

A blood substitute with a 10 gm % hemoglobin content is optimal for use as a resuscitative fluid or blood plasma expander because the 10 gm % concentration corresponds to the mass of red cells in blood (i.e., a hematocrit of 30 vol %) which is optimal for whole body oxygen delivery (calculated from arterial blood oxygen content x cardiac output). A 10 gm % solution of hemoglobin is oncotically active, has a lower viscosity than whole blood, and binds 1.34 cc of oxygen per gram of hemoglobin at ambient oxygen pressures.

Various properties of the canine-derived hemoglobin blood substitute are set out below in Table 1.

TABLE 1

| PROPERTY | VALUE |
|---|---|
| Total canine Hb concentration | 10 gm % |
| % methemoglobin | <1% |
| % carboxyhemoglobin | <0.5% |
| % sulfhydrylhemoglobin | Unknown |
| % nitrosylhemoglobin | Unknown |
| Colloid osmotic pressure | 40 mmHg |
| Viscosity | ≈2.0 cp |
| $P_{50}$ | 24 mmHg (pH 7.4) |
| Bohr coefficient | −0.54 ($\Delta logP_{50}/\Delta pH$) |
| Hill plot | Normal |
| Haldane effect | Normal |
| Davenport diagram | Normal |
| Oxygen content | 13.5 vol % |
| Oxygen capacity | 13.5 vol % |
| pH | 6.9 |
| $pCO_2$ | 15 mmHg |
| $PO_2$ | 200 mmHg |
| Na | 150 mmol/L |
| K | 3.4 mmol/L |
| $Ca^+$ | 1.2 mmol/L |
| Osmolality | 310 mosmol/kg |
| Dimers | Unknown |
| Monomer | Unknown |
| Free heme | Unknown |
| Free iron | Unknown |
| Trace metals | Unknown |

Results not presented in Table 1 are that methemoglobin levels were stable at ±0.4% for two weeks at 4° C. because the canine-derived hemoglobin blood substitute contained the original cytoplasmic methemoglobin-reducing enzyme, cytochrome $b_5$ reductase. While hemoglobin dimers, monomers and free heme were not measured, in vitro studies have shown that for hemoglobin concentrations of above about 1 to 2 gm % there is no detectable dissociation of hemoglobin tetramers [see Fanelli et al., Adv. Protein Chem., 19, 96–117 (1964)].

The following flow diagram illustrates the method sequence of the invention:

| | |
|---|---|
| STEP 1. | Collect blood from dog and suspend whole blood or packed cells in CPDA at 4° C. |
| ↓ | |
| RESULT 1. | Stored whole blood or packed red blood cells |
| STEP 2. | Separate, wash and pack erythrocytes |
| ↓ | |
| RESULT 2. | Washed, Packed Erythrocytes |
| STEP 3. | Mix erythrocytes with hypotonic buffer |
| ↓ | |
| RESULT 3. | Diluted extract of cytoplasm plus ghosts and partial ghosts |
| STEP 4. | Separate most ghosts/partial ghosts from diluted cytoplasm |
| ↓ | |
| RESULT 4. | First Supernatant: diluted extract of cytoplasm containing some ghosts/partial ghosts |
| STEP 5. | Adjust electrolytes of First Supernatant to produce isotonicity |
| ↓ | |
| RESULT 5. | Resealed ghosts/partial ghosts (reconstituted erythrocytes) plus diluted extract of cytoplasm |
| STEP 6. | Separate reconstituted erythrocytesfrom diiuted extract of cytoplasm |
| ↓ | |
| RESULT 6. | Diluted extract of cytoplasm plus few reconstituted erythrocytes and particulate matter (second supernatant) |
| STEP 7. | Separate residual erythrocytes and particulate matter from diluted cytoplasmic extract |
| ↓ | |
| RESULT 7. | Final product: a canine-derived hemoglobin blood substitute comprising uncontaminated cytoplasmic extract diluted in a pharmaceutically acceptable carrier medium |

While the present invention has been described in terms of preferred embodiments, it is understood that various modifications and variations will occur to those skilled in the art. For example, STEP 1 may not use adenine or, if processing is going to move directly from collection to processing without storage then a simple anticoagulant such as heparin can be used in place of the buffer. In STEP 2, the washing medium may be any isotonic solution such as phosphate-buffered saline but preferably will be pellet-promoting during STEP 4 centrifugation. In STEP 2, hetastarch is the key pellet-promoting compound but albumin (more expensive) may be used in its place. The pellet-promoting property of hetastarch or albumin is generated through their ability to behave as colloidal electrolytes which facilitate ionic bonding and cooperative hydrogen bonding between cell membranes to overcome the London dispersion charges that force cell membranes apart. One skilled in the art may find appropriate substitutions for the pellet-promoting wash medium, e.g., citrate-phosphate-dextrose buffer plus hetastarch or albumin. An essential point of the invention is to minimize disruption of the membrane's molecular organization and conserve the membrane and membrane-associated cytoskeletal macromolecules as shown by Bennett (see above FIG. A: Bennett, V., Physiological Reviews, 70:1029–1965, 1990). In STEP 3, the intention is to induce a nonporous→porous molecular phase transition within the membrane wall while conserving membrane and associated macromolecules, i.e., a "non-disruptive transition." In STEP 3, the transition can be induced preferably with a hypotonic buffer comprising 5 mM phosphate at pH 9.6. One skilled in the art, however, may achieve some of the non-disruptive transition with a pH greater than or equal to 8.0 but less than 9.6. The addition of minor compounds such as calcium or magnesium would be appropriate to ensure a successful non-disruptive transition when using a pH between 8.0 and 9.6. At STEP 3, the final hemoglobin concentration is preferably 11.0 to 11.5 gm %. Targeting for lower hemoglobin concentrations would enable a greater total yield but would compromise other properties, e.g., oxygen capacity, enzyme reducing systems and substrates. On the other hand, targeted concentrations approaching or exceeding 12 gm % would be considerably less enabling, e.g., the membrane transition would be less efficient, and the separation and yield would be compromised. In STEP 4, the separation is preferably accomplished with centrifugation, however, filtration may be used if disruption of the membranes is avoided. A second essential point of the invention is to restore the membranes to their native configuration. In STEP 5, this is accomplished by inducing the porous→non-porous molecular phase transition within the membrane wall. Restoring isotonicity through an adjustment of electrolyte concentration is one method of inducing the porous→non-porous transition. One skilled in the art could also use other reagents, compounds or physical conditions to induce the porous→nonporous transition. In STEP 6, the separation is preferably accomplished with centrifugation, however, one skilled in the art may use filtration if disruption of the membranes is avoided. In STEP 7, separation is preferably accomplished with filtration, however, one skilled in the art may use ultra-centrifugation if disruption of the membranes is avoided.

The canine-derived hemoglobin blood substitute was also tested in vivo on dogs for common adverse effects of therapeutic products which are administered intravascularly. The hemodilution protocol used and the physiologic tests performed are standard in the art and were similar to that described in Rabiner et al., *J. Exp. Med.*, 86, 455–463 (1967); Sunder-Plassmann et al., supra; and Crystal et al., *Anesth. Analg.*, 67, 211–218 (1988). Briefly, the hemoglobin product was infused into a venous access of an anesthetized dog with simultaneous withdrawal of arterial blood on a one-to-one basis at about 25 ml/minute until hematocrit was 50% of baseline (about 20 vol %). Tests for pyrogenic effects, hypotensive effects, arrhythmia, inotropic effects, bradycardia, tachycardia, hypovolemia, dysoria, and coagulopathy were all negative.

EXAMPLE 2

As discussed previously, use of a canine-derived hemoglobin blood substitute in place of a blood transfusion will cause hemodilution but will sustain blood pressure, cardiac output and oxygen delivery as is illustrated below.

Twelve dogs were hemodiluted with a canine-derived hemoglobin blood substitute prepared by methods of the present invention. Hemodilution with albumin of twelve dogs was performed as a control. Human albumin in normal saline was purchased as Albuminar-25 (25 mg %) from Armour Pharmaceutical Company (Kankakee, Ill.). The systemic and regional hemodynamic responses of the twenty-four dogs were then measured. The study was approved by the Loyola University Animal Care and Use Committee and performed in accordance with the National Research Council's Guide for the Use of Laboratory Animals.

Canine-derived Hemoglobin Blood Substitute Preparation

The canine-derived hemoglobin blood substitute (10%) was prepared as described in Example 1.

Surgical Preparation

Twenty-four conditioned, heartworm-free male mongrel dogs (20 to 30 kg) were anesthetized with sodium pentobarbital (30 mg/kg i.v.) followed by an i.v. maintenance dose of 4 mg/kg/hour. After intubation of the trachea with a cuffed endotracheal tube, the dog was mechanically ventilated (Siemens 900D Servoventilator) with 100% oxygen, tidal volumes of 10 to 12 ml/kg and respiration at a rate to achieve normocarbia. These settings were not changed throughout the study. Sodium bicarbonate was not administered. The body temperature of the dog was maintained at 39° C. with water-circulated heating pads.

The dog was placed supine and a polyethylene catheter (PE 200) was inserted into the thoracic aorta via the left femoral artery for measurement of blood pressure. Two small-bore (PE 90) heparin-filled catheters of different lengths were placed in the abdominal aorta via the right femoral artery to collect reference blood samples containing radioactive microspheres for measurement of regional blood flow. Wide-bore (PE 240) catheters were placed in the right femoral vein and in the right carotid artery, for isovolemic exchange transfusion and for the administration of intravenous fluids and collection of arterial blood samples. A 5 french thermodilution catheter was advanced into the pulmonary artery via the right external jugular vein for measurement of cardiac output and right atrial pressure. A Foley catheter was inserted into the bladder for urine collection.

Under fluoroscopy, a 5 french volume-conductance catheter (Mansfield Webster) was inserted via the left carotid artery across the aortic valve to the apex of the left ventricle to measure instantaneous volume. An 8/10 french Fogarty venous thrombectomy catheter was placed via the left femoral vein into the inferior vena cava just above the diaphragm to produce occlusive-unloading of the left ventricle over several cardiac cycles (20 seconds) during collection of pressure-volume data.

The dog was then placed on its right side and paralyzed with doxacurium (0.05 mg/kg) to perform a left thoracotomy in the fourth intercostal space. The exposed lung was retracted with gauze. Five cm $H_2O$ positive end-expiratory pressure was instituted to prevent atelectasis. A small incision was made in the pericardium near the left atrial appendage. The appendage was protracted and a PE 90 catheter, for microsphere injection, inserted into the ventricle via pressure verification and then pulled back into the atrium. A 3 french micromanometer-tipped pressure catheter (Millar) was then inserted via the appendage into the left ventricle for pressure recording. Both catheters were secured with a ligature around the appendage and distally taped to the animal. The exposed thoracic surface was covered with plastic film to prevent evaporation.

Measurements and Calculations

Continuous measurements of heart rate (HR), pulsatile aortic pressure, mean aortic pressure (MAP), left ventricular peak pressure (LVPP), rate-of-change of LVPP (dP/dt), LV end diastolic pressure (LVEDP), LV volume, and right atrial pressure (RAP) were recorded on an analog thermal array recorder (Gould Model TA4000) and stored on a computerized data acquisition system (Halcom, Inc.) Cardiac output (CO) was measured in triplicate using a Spectramed Hemoprol computer. Systemic vascular resistance (SVR) was calculated from (MAP-RAP)÷ CO. Systemic vascular hindrance (SVH) was calculated from SVR÷$\eta$, where $\eta$ is the apparent viscosity of blood in centipoise (cp). At high flow rates (shear rates ≅200 $s^{-1}$) assumed in the aorta, $\eta$ is 4.0 cp for hematocrit (Hct) of 40 vol % and 2.1 cp for Hct of 20 vol %. Stroke volume was derived from CO÷ HR. LV stroke work (LVSW) was calculated from (systolic AoP-LVEDP)× SV×0.0136.

Blood pH, $PCO_2$, $PO_2$ and $Na^+$, $K^+$ and $Ca^{++}$ concentrations were measured with a Nova Stat Profile 1 analyzer (Waltham, Mass.). Plasma colloid osmotic pressure (COP) was determined before and after hemodilution with a Wescor 4400 Colloid Osmometer (Logan, UH). The COP of 8% albumin was 39.3±0.9 mmHg. The COP of the canine-derived hemoglobin blood substitute was 40.8±1.0 mmHg. Hematocrit was determined volumetrically. Hemoglobin (gm %), methemoglobin (%) and percent oxygen saturation were measured with an Instrumentation Laboratories 482 CO-Oximeter (Lexington, Mass.). Hemoglobin oxygen content was measured with the cooximeter and added to the dissolved oxygen ($0.003\times PO_2$) to give total blood oxygen content (vol %).

Whole body oxygen extraction ratio ($O_2$ extr, %) was calculated from arteria-mixed venous oxygen content difference $C(a-v)O_2$ divided by the arterial oxygen content ($CaO_2$). Whole body oxygen consumption ($WBVO_2$) in ml/minute was determined using the Fick equation, $WBVO_2=CO\times C(a-v)O_2$. Oxygen delivery ($DO_2$) in ml/minute was calculated from $CaO_2\times CO$.

Catecholamines (pg/ml) were measured in arterial plasma using high-performance liquid chromatography with electrochemical detection (RAS 400 Liquid Chromatograph (West Lafayette, Ind.). Arterial plasma lactate concentrations (meq/L) were measured enzymatically with an Easy ST analyzer (E. Merck, Gibbstown, N.J.). Total blood volume was computed from plasma volume (indicator dilution of iodinated $I^{125}$-albumin, Mallinckrodt Medical, Inc., St. Louis, Mo.) and whole body hematocrit.

Regional Blood Flows and Distribution of Cardiac Output

Regional blood flows (ml/minute/100 g tissue) were measured with the reference isotope technique using 15$\mu$ microspheres as described in detail in Crystal et al., supra. Briefly, prior to injection, microspheres labeled with $Sc^{46}$, $Sr^{85}$, $Sn^{113}$ or $Ce^{141}$ were vortexed and sonicated. Approximately 30 microcuries ($1\times10^6$ microspheres) were injected into the left atrium of a dog. Beginning with each microsphere injection, duplicate reference blood samples were collected at a constant rate (6 ml $min^{-1}$) for 3 minutes from the femoral PE 90 catheters. Radioactivity of the duplicate samples differed by less than 10%, indicating adequate mixing of the microspheres in the left ventricular output. To maintain isovolemic conditions during reference sampling, a 5% albumin solution was infused simultaneously.

After the final injection of microspheres, the heart was stopped by intravenous injection of potassium chloride. Skin and bone (rib) were sampled from a shaved area distal to the thoracotomy. Skeletal muscle samples were taken from the hind limb, back, forelimb and head. The GI tract was excised from the esophageal sphincter to the anus. All mesentery and omentum were trimmed. The stomach was separated from the tract. These and all other organs were weighed. Multiple samples were taken from each organ and transferred to a tared counting tube.

The tissue and reference samples were weighed and analyzed for radioactivity with a gamma scintillation counter equipped with a multichannel analyzer (Packard Instrument, Downers Grove, Ill.). Isotope separation was accomplished by standard techniques of gamma spectroscopy. Values for organ blood flows ($BF_{organ}$) in ml $min^{-1}$ were calculated from the equation $BF_{organ}=ABF\times(MC\div AC)\times$organ weight (g), where ABF is the rate of arterial reference sampling (ml/minute), MC is the microsphere radioactivity (counts $min^{-1}$ $g^{-1}$) in the tissue samples, and AC is the total microsphere radioactivity (counts/minute) in the arterial reference samples. The fractional distribution of cardiac output to each organ was computed from $BF_{organ}\div\Sigma BF_{organ}$, where $\Sigma BF_{organ}$ is the sum of all organ flows. Skeletal muscle, skin and bone weights were calculated as 40%, 9% and 8% of body weight, respectively.

Left Ventricular End-Systolic Elastance ($E_{es}$)

Left ventricular contractility was determined from end-systolic elastance (Ees) using pressure-volume relationships according to the methods of Kass et al., *Circulation*, 79, 167–178 (1989). Briefly, a catheter with 11 electrodes spaced 1 cm from its distal end was positioned in the ventricle so that its tip was at the apex (verified with fluoroscopy). A weak electrical field (20 KHz, 0.03 mA RMS current) was generated through the LV cavity from the electrodes at the apex and at the aortic valve. Conductances measured between pairs of electrodes within the field provided a volume conductance measurement that includes the actual ventricular volume plus an offset volume dependent on structures surrounding the ventricular cavity (LV tissue, RV tissue and blood, and juxta-pericardial tissue). The offset volumes were ignored because only relative volume changes, not absolute volume measurements, were considered in the final analysis.

The volume signals were processed by a Leycom Sigma 5 signal conditioner (Stitching, Holland). An inferior vena caval occlusion varied preload to the heart, during which the first 10–15 cardiac cycles (or pressure-volume loops) were collected. As preload decreased the area of each loop decreased. An algorithm was then used to find the end-systolic pressure-volume point of each loop. A linear regression line through each point determined an equation, the end-systolic pressure-volume relationship (ESPVR). The slope of the ESPVR, called the end-systolic elastance ($E_{es}$), is a load independent measure of global left ventricular contractility. Increases and decreases in $E_{es}$ correspond to increases and decreased in contractility, respectively. Limitations to this technique: the conductance offset volume could potentially change from cardiac cycle to cardiac cycle during an occlusion thus skewing the ESPVR in one direction or another. To test for this error we made slow (20 second) and fast (5 second) occlusions during either end-inspiratory or endexpiratory pauses. We found no difference in the measured $E_{es}$ values determined in this manner.

Experimental Protocol

Upon arrival in the laboratory, typically all dogs had hematocrits of 45 vol % or greater and filling pressures (LVEDP) of 5 mmHg or less. Following cannulation, all dogs were hydrated with 5 gm % albumin to increase filling pressure (LVEDP) above 5 mmHg and to bring hematocrit to near 40 vol %. Twelve dogs underwent isovolemic exchange of blood for 10 gm % hemoglobin to hematocrit 50% of baseline. Twelve more dogs were exchanged transfused with 8 gm % albumin in order to compare effects of hemodilution with a hemoglobin-based blood substitute to those of hemodilution with an inert colloid having a comparable molecular weight (both hemoglobin and albumin have molecular weights of about 65,000). The colloid pressure of 10 gm % hemoglobin and 8 gm % albumin (both about 40 Torr) is about twice that of dog plasma and after in vivo dilution would be expected to sustain plasma volumes at baseline values or greater. The smaller weight fraction of albumin needed to obtain a colloid pressure similar to hemoglobin is due to differences in surface charge, molecular shape, intermolecular association and hydration properties of the two colloids.

Hemodilution was produced by a simultaneous isovolemic exchange of blood for the canine-derived hemoglobin blood substitute or for the albumin solution (rate of 20 ml/minute, about 45 ml/kg). Following the exchange all measurements and samples were obtained within 30 minutes.

Effects of Hemodilution with Albumin Solution

Figure 3A:
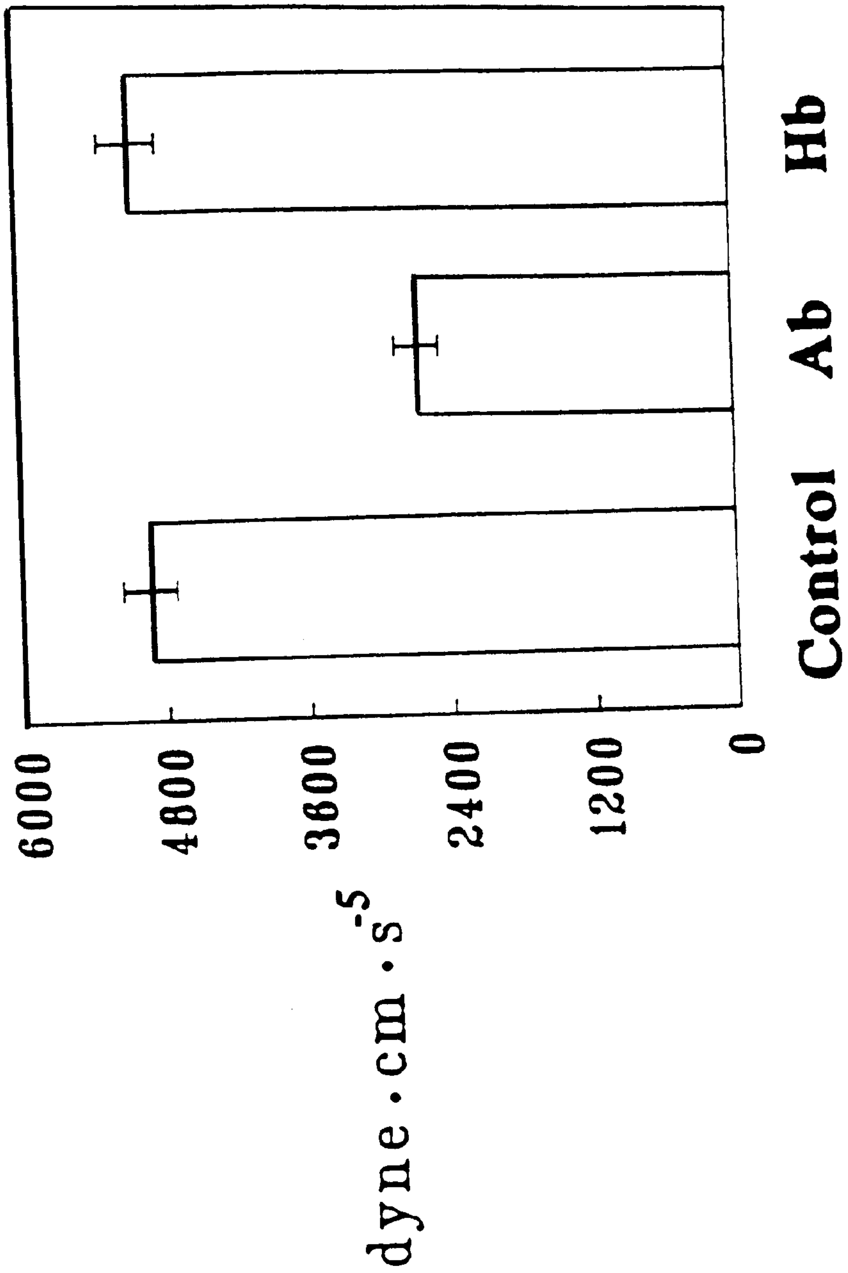
FIG. 3A is a bar graph representing the systemic vascular resistance (dyne·cm·$s^{-5}$) of control baseline, albumin-hemodilution (AB), and hemoglobinhemodilution (Hb) in mongrel dogs.
Figure 3B:
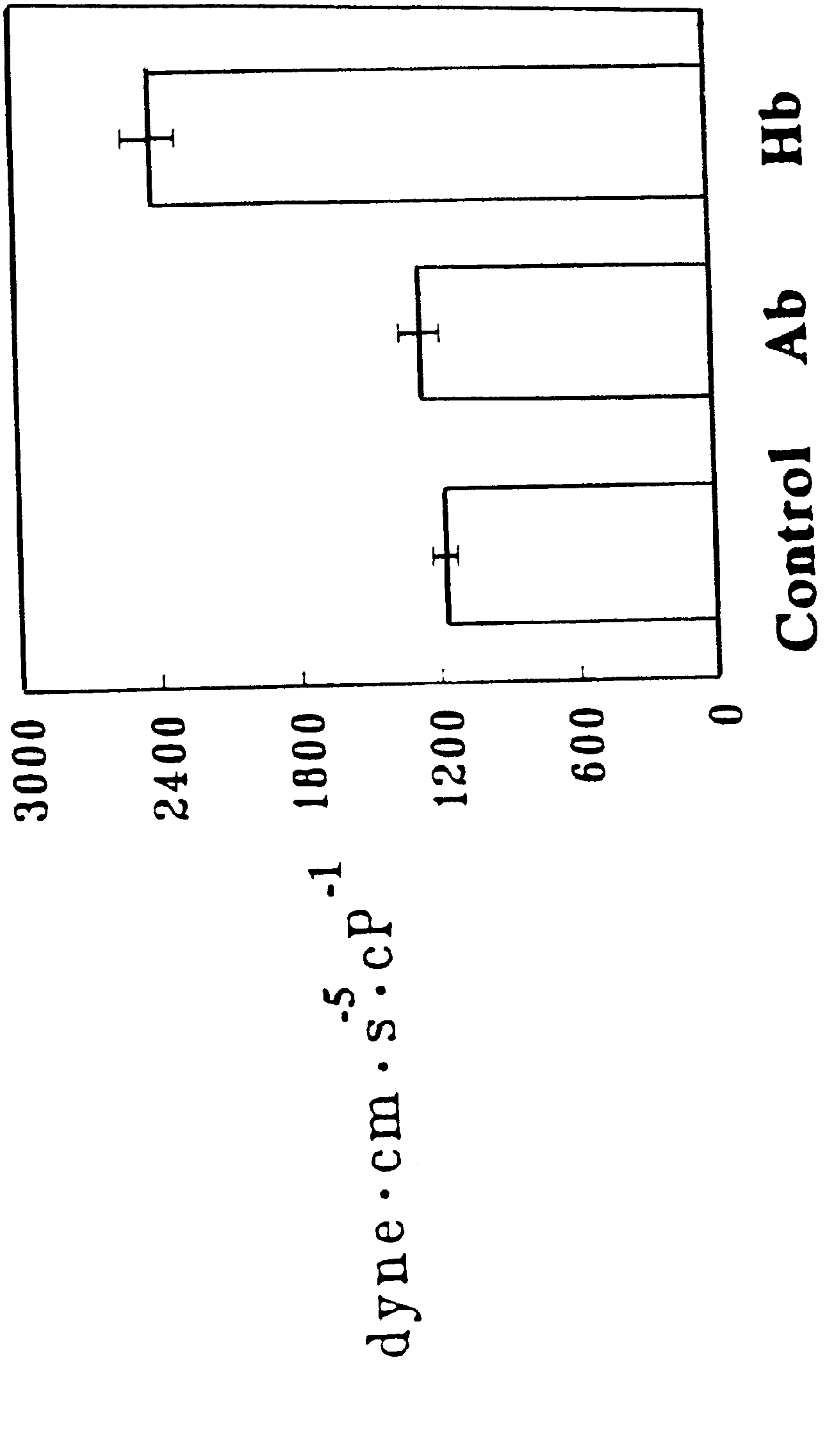
FIG. 3B is a bar graph representing the systemic vascular hindrance (dyne·cm·$s^{-5}$·$cP^{-1}$) of control baseline, albumin-hemodilution (AB), and hemoglobin-hemodilution (Hb) in mongrel dogs.

Hemodilution with albumin to a hematocrit 50% of control (20±1 vol %) caused cardiac output to increase to approximately 177% of control as is shown in FIGS. 1A–1D. Proportional increases occurred in stroke volume as heart rate did not change. Left ventricular stroke work increased markedly. (See Table 2 below) Hemodilution reduced systemic vascular resistance to about 54% of control but did not change systemic vascular hindrance (FIGS. 3A–3B). Mean aortic, right atrial and LV end-diastolic pressures were not changed. Thus the reduction in systemic vascular resistance was directly proportional to the apparent decrease in viscosity (assumed 50% of control) rather than to changes in arteriolar tone. Stroke volume and cardiac output increased because the viscosity component of afterload was reduced allowing more complete emptying of the ventricle.

TABLE 2

| Variable | Control n = 24 | AbHD n = 12 | HbHD n = 12 |
|---|---|---|---|
| MAP (mm Hg) | 134 ± 3 | 122 ± 4 | 136 ± 6 |
| LVPP (mm Hg) | 153 ± 3 | 150 ± 3 | 154 ± 6 |
| LV dP/dtmax (mm Hg/sec) | 1669 ± 88 | 1753 ± 137 | 1713 ± 76 |
| LV Elastance (mm Hg ml) | 4.78 ± 0.27 | 5.26 ± 0.35 | 4.91 ± 0.58 |
| LVSW (g m/beat) | 27.9 ± 1.5 | 45.3 ± 3.5 | 29.2 ± 3.4 |
| heart rate (beats/min) | 160 ± 4 | 167 ± 6 | 153 ± 5 |
| Blood Volume (ml) | 1885 ± 81 | 1856 ± 102 | 1892 ± 125 |

Hemodilution with albumin caused an approximate 50% reduction in hemoglobin concentration (14.7±0.3 to 7.0±0.2 g/100 ml) and arterial oxygen content (19.7±0.4 to 10.0±0.2 ml/100 ml) (See Tables 3 and 4). The arterial-mixed venous oxygen content difference decreased 47% while oxygen extraction ratio was unchanged. Total body oxygen delivery and whole body oxygen consumption were not changed from control values. Arterial blood gases, electrolytes and plasma catecholamines were within the control range (See Table 3 and Table 5 below). Hemodilution with hyperoncotic 8 gm % albumin caused plasma colloid osmotic pressure to increase 20% yet there was no significant increase in blood volume. (See Tables 2 and 3)

TABLE 3

| Parameter | Control n = 24 | AbHD n = 12 | HbHD n = 12 |
|---|---|---|---|
| pH | 7.39 ± 0.01 | 7.35 ± 0.01 | 7.38 ± 0.01 |
| $PCO_2$ (mm Hg) | 35 ± 1 | 37 ± 2 | 34 ± 2 |
| $PO_2$ (mm Hg) | 390 ± 21 | 439 ± 33 | 411 ± 31 |
| Hematocrit (vol %) | 42 ± 1 | 20 ± 1 | 21 ± 1 |
| $Na^+$ (mmol/L) | 151 ± 1 | 152 ± 1 | 152 ± 1 |
| $K^+$ (mmol/L) | 3.4 ± 0.1 | 3.3 ± 0.1 | 3.7 ± 0.2 |
| $C^{++}$ (mmol/L) | 1.27 ± 0.02 | 1.17 ± 0.03 | 1.15 ± 0.05 |
| Total Hb (g/100 ml) | 14.7 ± 0.3 | 7.1 ± 0.2 | 11.5 ± 0.5 |
| Total MetHb (%) | 0.8 ± 0.04 | 0.8 ± 0.06 | 0.8 ± 0.07 |
| Plasma Hb (g/100 ml) | — | — | 4.6 ± 0.2 |
| Plasma MetHb (%) | — | — | 1.5 ± 0.16 |
| Plasma COP (mm Hg) | 18.7 ± 0.6 | 22.5 ± 0.7 | 22.8 ± 0.8 |

TABLE 4

| Parameter | Control n = 24 | AbHD n = 12 | HbHD n = 12 |
|---|---|---|---|
| $CaO_2$ (ml/100 ml) | 19.7 ± 0.4 | 10.0 ± 0.2 | 14.9 ± 0.4 |
| $CvO_2$ (ml/100 ml) | 14.2 ± 0.6 | 6.8 ± 0.5 | 8.8 ± 0.6 |
| $C(a-v)O_2$ (ml/100 ml) | 5.1 ± 0.3 | 2.7 ± 0.4 | 6.1 ± 0.4 |
| $O_2$ extr (%) | 27 ± 3 | 30 ± 2 | 45 ± 3 |
| $DO_2$ (ml/min) | 434 ± 18 | 418 ± 25 | 302 ± 22 |
| $WBVO_2$ (ml/min) | 122 ± 8 | 126 ± 10 | 125 ± 11 |

TABLE 5

| Parameter | Control | AbHD | HbHD |
|---|---|---|---|
| Norepinephrine pg/ml, n = 8 | 114 ± 7 | 106 ± 6 | 125 ± 12 |
| Epinephrine pg/ml, n = 8 | 217 ± 18 | 249 ± 19 | 219 ± 14 |
| Lactate meg/L, n = 6 | 1.4 ± 0.2 | — | 2.2 ± 0.3 |

Compared to control blood flows, regional blood flows after hemodilution with albumin were significantly increased (about 80%) through various organ beds [see Table 6: regional blood flows (ml/minute) and fraction of cardiac output (% CO) in the kidney, gastrointestinal tract (GI), spleen, pancreas, liver arteries (hepatic), lung arteries (bronchial), skeletal muscle (muscle), skin, bone, right (R) ventricle, left (L) ventricle, septum and brain of control baseline and albumin-hemodilution (AbHD) in mongrel dogs].

The increased flows in the kidney, GI tract (stomach, small and large intestine, colon), liver (hepatic artery), lung (bronchial), skeletal muscle, skin, bone and brain were in approximate proportion to the increased cardiac output. There was, however, a redistribution of flow during hemodilution from the spleen, which received a smaller fraction of the cardiac output, to the heart which received a greater fraction of the cardiac output.

TABLE 6

| | Control | | AbHD | |
|---|---|---|---|---|
| Organ | Blood Flow | % CO | Blood Flow | % CO |
| Kidney | 634 ± 34 | 31.1 ± 1.1 | 997 ± 72* | 28.0 ± 0.9 |
| GI tract | 37 ± 3 | 12.7 ± 0.8 | 82 ± 5* | 15.3 ± 0.7 |
| Spleen | 163 ± 18 | 5.8 ± 0.5 | 186 ± 27 | 3.5 ± 0.3* |
| Pancreas | 21 ± 2 | 0.5 ± 0.1 | 52 ± 5* | 0.6 ± 0.1 |
| Hepatic | 33 ± 3 | 9.4 ± 0.7 | 70 ± 5* | 9.5 ± 0.6 |
| Bronchial | 64 ± 12 | 9.2 ± 2.2 | 177 ± 50* | 9.0 ± 2.1 |
| Muscle | 2.9 ± 0.2 | 13.5 ± 1.2 | 7.1 ± 0.3* | 14.2 ± 0.7 |
| Skin | 2.5 ± 0.2 | 2.4 ± 0.2 | 6.6 ± 0.7* | 2.7 ± 0.3 |
| Bone | 11.5 ± 1.1 | 9.4 ± 0.9 | 22.0 ± 1.8* | 9.4 ± 0.6 |
| R Vent | 56 ± 3 | 0.9 ± 0.1 | 178 ± 17* | 1.6 ± 0.2* |
| L Vent | 93 ± 4 | 3.4 ± 0.2 | 283 ± 25* | 5.4 ± 0.4* |
| Septum | 86 ± 5 | 1.1 ± 0.1 | 270 ± 22* | 2.7 ± 0.2* |
| Brain | 32 ± 2 | 1.4 ± 0.2 | 82 ± 6* | 1.5 ± 0.1 |

Effects of Hemodilution with the Canine-Derived Hemoglobin Blood Substitute

When hematocrit was reduced to 50% of control the blood substitute, stroke volume did not change from control values (see FIGS. 1A–1D).

Similar to hemodilution with albumin, systemic pressures were not changed from control values (see FIGS. 2A–2D and Table 2). Despite a decrease in apparent viscosity similar to albumin hemodilution (assumed 50% of control), systemic vascular resistance was not changed from control values, however, systemic vascular hindrance increased almost 100% (see FIGS. 3A–3B). Left ventricular elastance and other hemodynamic parameters were not changed from control values. Thus, stroke volume and cardiac output were not increased because the decreased viscosity component of afterload was offset by the increased hindrance component (SVH).

Whole blood hemoglobin concentration decreased only 22% during hemodilution with the canine-derived hemoglobin blood substitute (from 14.7±0.3 to 11.5±0.5 g/100 ml). Plasma hemoglobin (4.6 g/100 ml) comprised approximately 40% the total whole blood hemoglobin concentration (see Table 2). Arterial oxygen content decreased only 24% (from 19.7±0.4 to 14.9±0.4 ml/100 ml) (see Table 4). Despite the additional oxygen supplied by plasma hemoglobin, hemodilution and the unchanged cardiac output resulted in a 30% decrease in oxygen delivery. However, a 60% increase in oxygen extraction ratio maintained oxygen consumption at baseline levels (Table 4). Arterial pH, electrolytes and plasma catecholamines were unchanged from control levels.

Total blood methemoglobin was not changed significantly from control, although the infused hemoglobin (plasma) had a greater percentage of methemoglobin (see Table 2). The plasma methemoglobin level was not significantly different from that of the canine-derived hemoglobin blood substitute. Arterial blood gases and electrolytes remained within the control range. Again, similar to the albumin solution, the hyperoncotic hemoglobin blood substitute caused plasma colloid osmotic blood pressure to increase approximately 22% yet there was no significant change in blood volume (see Tables 2 and 3). Some plasma hemoglobin dissociation was evident by the presence of hemoglobin in the urine (hemoglobinuria). The amount excreted varied but was always less than 1% of the approximately 100 grams hemoglobin infused.

Changes in regional blood flows were measured and the results are presented below in Table 7 [regional blood flows (ml/minute) and fraction of cardiac output (% CO) in the kidney, gastrointestinal tract (GI), spleen, pancreas, liver arteries (hepatic), lung arteries (bronchial), skeletal muscle (muscle), skin, bone, right (R) ventricle, left (L) ventricle, septum and brain of control baseline and hemodilution with the hemoglobin blood substitute in mongrel dogs] and Table 8.

TABLE 7

| | Control | | OxyHbHD | |
|---|---|---|---|---|
| Organ | Blood Flow | % CO | Blood Flow | % CO |
| Kidney | 577 ± 38 | 32.9 ± 1.8 | 492 ± 45 | 27.5 ± 2.3 |
| GI tract | 34 ± 3 | 11.7 ± 0.7 | 37 ± 3 | 12.9 ± 0.7 |
| Spleen | 162 ± 19 | 5.2 ± 0.6 | 152 ± 34 | 5.1 ± 0.8 |
| Pancreas | 24 ± 4 | 0.6 ± 0.1 | 27 ± 3 | 0.6 ± 0.1 |
| Hepatic | 35 ± 7 | 8.3 ± 1.1 | 27 ± 5 | 6.8 ± 1.1 |
| Bronchial | 59 ± 10 | 7.0 ± 1.4 | 39 ± 6* | 3.4 ± 0.7* |
| Muscle | 3.1 ± 0.4 | 13.5 ± 1.1 | 5.3 ± 0.7* | 21.1 ± 1.5* |
| Skin | 2.5 ± 0.5 | 2.2 ± 0.2 | 3.3 ± 0.4 | 2.8 ± 0.2 |
| Bone | 13.9 ± 1.5 | 10.5 ± 1.2 | 11.4 ± 1.8 | 8.4 ± 1.0 |
| R Vent | 52 ± 4 | 0.9 ± 0.1 | 99 ± 9* | 1.4 ± 0.1* |
| L Vent | 92 ± 7 | 3.7 ± 0.4 | 173 ± 16* | 6.3 ± 0.5* |
| Septum | 80 ± 7 | 1.2 ± 0.1 | 174 ± 20* | 2.1 ± 0.2* |
| Brain | 27 ± 1 | 1.3 ± 0.1 | 42 ± 3* | 1.7 ± 0.2 |

TABLE 8

| ORGAN BLOOD FLOW | CHANGE FROM CONTROL |
|---|---|
| Renal | No |
| Gastrointestinal | No |
| Spleen | No |
| Pancreas | No |
| Liver | No |
| Bronchial | Yes (−33%) |
| Skin | No |
| Bone | No |
| Skeletal muscle | Yes (+71%) |
| Myocardium | Yes (+80%) |
| Brain | Yes (+40%) |
| Total (= Cardiac output) | No |

Thus, in contrast to hemodilution with albumin, hemodilution with the canine-derived hemoglobin blood substitute did not augment cardiac output yet produced a sustained output comparable to control baseline. Furthermore, in contrast to the prior art, the canine-derived hemoglobin blood substitute did not produce hypertension. Blood volume was not affected by the canine blood substitute, yet another difference from the prior art which claims decreases in blood volume with non-polymerized hemoglobin blood substitutes. Oxygen delivery was not adversely affected by hemodilution with the blood substitute and was comparable to baseline. As Table 7 shows, a fraction of the cardiac output was redistributed to skeletal and heart muscle (myocardium) from bronchial tissue and, although not statistically significant, possibly a minor redistribution from kidney, liver and bone. In conclusion, the canine-derived hemoglobin blood substitute of the present invention was a safe and useful alternative to blood transfusion in dogs, however, it was especially effectual at inducing accelerated oxygen delivery to muscle tissue (skeletal and heart). The invention, thus, revealed as specific use for the canined-erived blood substitute, i.e., as a selective perfusion fluid to oxygenate skeletal muscle and heart muscle without inducing hypertension or decreases in blood volume.

While the present invention has been described in terms of preferred embodiments, it is understood that various modifications and variations will occur to those skilled in the art.

What is claimed is:

1. A method for producing a hemoglobin blood substitute by performing the following steps under sterile conditions:

a) washing a first volume of erytirocytes with saline-hetastarch solution at a pH 7.4 and packing said erythrocytes by centrifugation at 1500 g for 20 minutes;

b) adding a second volume of cold dibasic sodium phosphate buffer at pH of about 9.6, wherein the said second volume being not more then twice of the said first erythrocyte volume, and wherein the hemoglobin mixture formed has hemoglobin concentration of about 11.5 gm %;

c) stirring the mixture slowly for at least 10 minutes;

d) centrifuging the mixture of the step c) and isolating a first supernatant;

e) adding sufficient physiological electrolyte to the supernatant of step (d) to result in isotonic concentration so that the color of the said first supernatant is transformed from dark cherry red to opaque bright red;

(f) centrifuging the mixture of step (e);

(g) isolating second supernatant of step (f) consisting essentially of 100% cytosomal material diluted in a buffer, said supernatant being translucent dark cherry red; and (h) passing second supernatant through a filter of 0.25 $\mu$M or less pore size to produce the hemoglobin blood substitute.

2. The method of claim 1, wherein the hemoglobin blood substitute is derived from canine erythrocytes.

3. The method of claim 1, wherein the hemoglobin blood substitute is derived from human or bovine or ovine erythrocytes.

4. The method of claim 1, wherein said step (a) comprises serial washings with phosphate-buffered saline—6% hetastarch solution at a pH of about 7.4.

5. The method of claim 1, wherein said step (d) comprises centrifugation at 28,000 g for at least 2.5 hours at 4° C., and wherein step (f) comprises centrifugation at 28,000 g for about 1 h at 40° C.

6. The method of claim 1, wherein the physiologic electrolyte at step (e) is sodium chloride added to final concentration of about 150 mM.

7. The method of claim 6 wherein about 3 mM potassium chloride and about 1.5 mM calcium chloride are additionally added.

8. The method of claim 1, wherein step (h) is serially passing second supernatant through a 5.0$\mu$ filter, a 1.0$\mu$ filter, a 0.45$\mu$ filter and a 0.25$\mu$ filter at a flow rate of about 250 ml/min.

* * * * *

UNITED STATES PATENT AND TRADEMARK OFFICE

CERTIFICATE OF CORRECTION

Figures 4A, 4B:
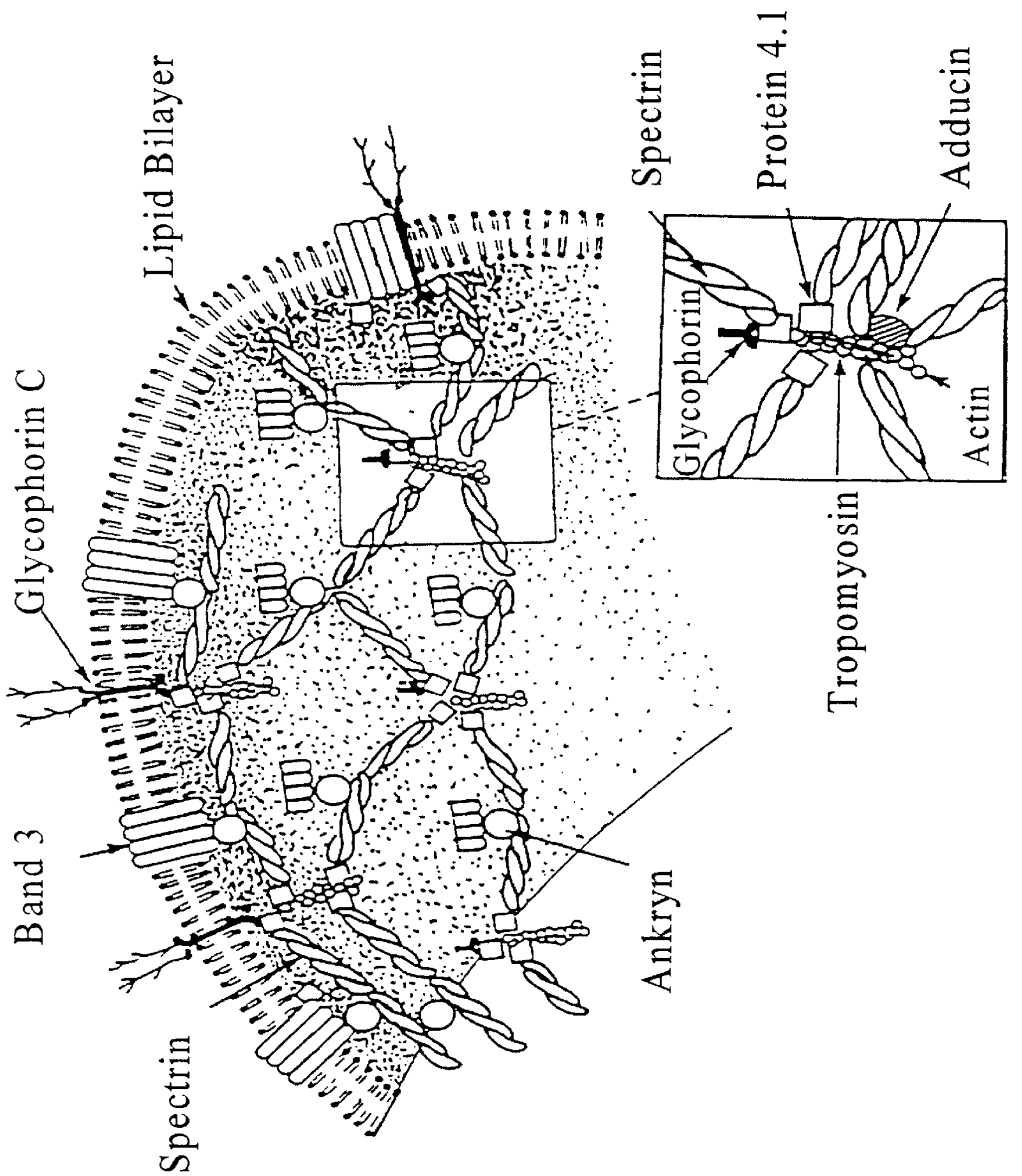
FIG. 4A is a macromolecular depiction of the spectrin-actin junction with associated regulatory proteins that together modulate membrane shape and function. From Bennett, V.: Spectrin-based membrane skeleton: A multipotential adaptor between plasma membrane and cytoplasm. Physiol. Rev., 70:1029–1965, 1990.
FIG. 4B is an overview of the erythrocyte membrane macromolecular composite. From Bennett, V.: Spectrin-based membrane skeleton: A multipotential adaptor between plasma membrane and cytoplasm. Physiol. Rev., 70:1029–1965, 1990.

PATENT NO. : 6,005,078
DATED : December 21, 1999
INVENTOR(S) : Michael William Rooney It is certified that error appears in the above-identified patent and that said Letters Patent is hereby corrected as shown below:

| Column | Line | Correction | | |
|---|---|---|---|---|
| 5 | 63 | mmhg | to | mmHg |
| 6 | 38 | citratephosphate | to | citrate-phosphate |
| 6 | 41 | grampositive | to | gram-positive |
| 7 | 10 | FIG.A | to | FIG.4A |
| 7 | 37 | which then, as reconstituted erythrocytes, refract light | | |
| 14 | 35 | 7.0 ±0.2 | to | 7.1 ±0.2 |
| 15 | 60 | *, significantly different form Control ($p<0.05$) | | |
| 16 | 67 | *, significantly different form Control ($p<0.05$) | | |
| 17 | 28 | output was redistributed to brain and to skeletal | | |
| 17 | 35 | oxygen delivery to brain and to muscle tissue | | |
| 17 | 47 | eryircytes | to | erythrocytes |
| 18 | 28 | substitute is derived from human or cat or bovine or | | |
| 18 | 35 | C., | to | C, |

Signed and Sealed this

Tenth Day of July, 2001

Nicholas P. Godici

Attest:

NICHOLAS P. GODICI

*Attesting Officer* *Acting Director of the United States Patent and Trademark Office*